(12) United States Patent
Volfkovich et al.

(10) Patent No.: US 7,059,175 B2
(45) Date of Patent: Jun. 13, 2006

(54) POROSIMETRIC DEVICE

(75) Inventors: Yury Mironovich Volfkovich, Moscow (RU); Igor Alexandrovich Blinov, Moscow (RU); Aleksandrs V. Sakars, Toronto (CA)

(73) Assignee: Porotech Ltd., Vaughan (CA)

( * ) Notice: Subject to any disclaimer, the term of this patent is extended or adjusted under 35 U.S.C. 154(b) by 28 days.

(21) Appl. No.: 10/884,947

(22) Filed: Jul. 7, 2004

(65) Prior Publication Data

US 2005/0034507 A1 Feb. 17, 2005

Related U.S. Application Data

(60) Provisional application No. 60/484,645, filed on Jul. 7, 2003.

(51) Int. Cl.
*G01N 15/08* (2006.01)

(52) U.S. Cl. ............................................. 73/38
(58) Field of Classification Search ................. 73/38
See application file for complete search history.

(56) References Cited

U.S. PATENT DOCUMENTS

| | | | | |
|---|---|---|---|---|
| 2,104,047 | A | * | 1/1938 | Kendall ............................ 73/38 |
| 2,345,535 | A | * | 3/1944 | Horner ............................ 73/38 |
| 3,345,880 | A | * | 10/1967 | Dietmar ......................... 73/866 |
| 4,660,412 | A | | 4/1987 | Gupta |
| 6,298,711 | B1 | * | 10/2001 | Volfkovich et al. ............. 73/38 |
| 6,327,892 | B1 | * | 12/2001 | Koiso et al. ..................... 73/38 |
| 6,655,192 | B1 | * | 12/2003 | Chavdar ......................... 73/38 |

OTHER PUBLICATIONS

The Method of Standard Porosimetry—Investigation of the formation of porous structures—Volfkovich and Bagotzky—A.N. Frumkin Institute of Electrochemistry, 117071 Moscow Russian Federation.

(Continued)

*Primary Examiner*—Hezron Williams
*Assistant Examiner*—John Fitzgerald
(74) *Attorney, Agent, or Firm*—Marks and Clerk; Richard J. Mitchell

(57) ABSTRACT

A porosimetric device is disclosed for studies of physico-chemical properties of materials, in particular for study of the pore structure. The device comprises a balance, a clamping device for keeping the standard and the porous sample(s) in contact (the standard and the porous sample(s) containing wetting liquid inside their pores), an automatic manipulator for moving the sample frames, several drying stations for drying a number of samples simultaneously, automatic flowmeter valves for the drying gas, electric and pneumatic drives for the manipulator and the valves. Each drying station is placed at sufficient distance from the balance thereby enabling heating of the samples without heating the balance. The drying process is carried out by gas, which is heated up in special heaters. The manipulator has two degrees of freedom. It can perform vertical movements for placing samples and standards on the balance as well as horizontal movement between the drying stations and the balance. The porosimeter includes a gripper for sample frames, vertical servo-drives for each drying station, which provide vertical positioning of the sample frames when gripped, and a cap or a cylinder closed from the top, which tightly covers each sample and standard before weighing, thereby essentially reducing the evaporation of measuring liquid or condensation of moisture within the sample pores.

16 Claims, 5 Drawing Sheets

OTHER PUBLICATIONS

The Method of Standard Porosimetry—Principles and possibilities—Volfkovich and Bagotzky—A.N. Frumkin Institute of Electrochemistry, 117071 Moscow Russian Federation.

Physical Chemistry of Surfaces—6th Edition Arthur W. Adamson—Chemistry, U of Southern California, Los Angeles, CA and Alice Gast—Chemical Engineering Stanford U. CA—John Wiley & Sons, Inc.

XVI The Solid-Gas Interface—Methods Requiring Knowledge of the Surface Free Energy or Total Energy.

Adamson, A.W., Physical Chemistry of Surface, John Wiley & Sons Publ., New York, 1976.

Volfkovich, Yu.M. and Bagotzky, V.S., J. Power Sources, 48(1994)327, 339.

* cited by examiner

POROSIMETRIC DEVICE

CROSS REFERENCE TO RELATED APPLICIATION

This invention claims the benefit under 35 USC 119(e) of prior U.S. provisional application No. 60/484,645 filed Jul. 7, 2003, the contents of which are incorporated herein by reference.

FIELD OF THE INVENTION

The present invention relates generally to devices for the study of physicochemical properties of materials, and in particular to porosimetric devices for the study of the structure of porous materials.

DESCRIPTION OF THE PRIOR ART

Devices for studies of the porous structure of materials are known in the art. In general, they employ intrusion of non-wetting liquid, namely mercury, into pores of a sample, and are known as mercury porosimeters (N. L. Ritter, L. C. Drake, Ind. Eng. Chem. Analit. Ed., 17, 787, 1945; USSR Inventors Certificate No. 104315, 1952 G 01 N 15/08).

The mercury porosimeters, which are the most widespread porosimetric devices, permit measurement of pore distribution within the pore size range from 2 to $10^5$ nm. However, measurements accomplished within the pore-size range from 2 to 7 nm require applying very high pressure (up to 4000 ATM) to intrude mercury into sample pores, which complicates of the device. Under pressures of thousands ATM, deformation and destruction of the most of samples can occur. Besides, it is impossible to use mercury porosimeters for investigation of substances, which chemically react with mercury (amalgamation). In addition, when mercury porosimeters are used, the value of the wetting angle of mercury with the most of samples is unknown. However, this value is used for calculation of the radii of the pores.

In practice, various materials are measured using some average value of this wetting angle, which entails significant errors in measurements.

An important disadvantage of mercury porosimeters is the fact that they use a substantial amount of very toxic substance, mercury.

Also known in the art are devices for measurement of the porous structure of a substance using capillary condensation, for instance adsorption apparatus (A. W. Adamson, Physical Chemistry of Surface, John Wiley & Sons Publ., New York, 1976). However, devices operating by the capillary condensation method provide sufficient accuracy measurement of pore distribution only within the radius range from 1 to 50 nm.

Still known in the art is a three-fluid method of non-mercury liquid intrusion porosimetry (U.S. Pat. No. 4,660, 412). The sample to be tested and a given amount of a non-wetting intrusion liquid, other than mercury, are introduced into a sealable, pressurizable chamber, the sample placed above the intrusion liquid. The chamber is sealed and evacuated. An intermediate pressurizing liquid, such as mercury, is introduced into the chamber and pressurized by primary pressurization liquids, such as alcohol or oil, so as to force the intrusion liquid into the pores of the sample. The volume of intermediate pressurization liquid introduced into the chamber is measured as the pressure increases incrementally to establish the pore distribution of the sample.

Drawbacks of this method, as well as the method of mercury porosimetry, are the deformations of the studied samples structure under the action of high pressure of non-wetting liquids, and, as a rule, the varying or unknown values of wetting angles of the liquid in contact with the test materials.

Still known in the art is a device for measurement of characteristics of porous bodies by the method of standard porosimetry (USSR Inventors Certificate No. 543852, 1975, G01N15/08; Yu. M. Volfkovich, V. S. Bagotzky, J. Power Sources, 48 (1994) 327, 339). This device measures the equilibrium dependence liquid content, i.e. the volume of liquid in the sample as a function of the volume of liquid in the standard. Prior to the measurement, the integral liquid distribution for the standard is established. The amount of liquid in the sample(s) is determined by weighing. The porous standards and sample(s) are prepared in the shape of discs with thickness of 0.1–3 mm. They are washed, dried, and weighed. Then they are filled with the liquid (under vacuum). The stack of discs is assembled in a special clamping device in which they are tightly attached to one another for attainment of capillary equilibrium. In the assembly, the sample is usually placed between two standards. A small portion of the liquid is evaporated off this assembly through the open surface by heating and/or vacuum treatment. When certain amount of liquid is removed, the open surface of the samples is hermetically covered and left undisturbed for a certain time to allow the establishment of a new capillary equilibrium. Subsequently, the stack is disassembled; the samples are placed into individual vials and weighed. Then the stack is reassembled and all operations repeated several times until the liquid from the test sample is completely evaporated. To obtain a porosimetric curve, it is necessary to perform this set of operations 15 to 50 times depending on the required accuracy of measurement. All these manipulations lead to labor intensity and prolonged measurement process.

An apparatus for measurement by the method of the standard porosimetery comprises a balance; a clamping device, which keeps in contact the standards and the sample(s); a soaking chamber; a drying vessel; a vacuum pump; and a heater.

All the above devices known in the art do not provide quick accurate results and are not applicable for maximal range of the pores radii; the process of measurement is prolonged and laborious.

U.S. Pat. No. 6,298,711 discloses an automated standard porosimeter developed on the basis of the Method of Standard Porosimetry (MSP). The porosimeter disclosed in this patent comprises a balance; a device for keeping the standards and sample(s) in tight contact with each other, said standards and samples containing a wetting liquid in their pores; an automatic manipulator consisting of a body, a frame and a motor connected through a transmission with the frame, said frame being provided with a spring and a support, while the device for keeping the standards and the sample(s) in tight contact comprises a drying device connected to the body, and yokes having apertures to provide contact between the porous samples, said yokes having catches.

Drawbacks of this Porosimeter are: inability to study samples with ultra-micropores due to the impossibility to evaporate liquid from such pores using gas at ambient temperature; short life span of the standards due to their handling; insufficient accuracy of the measurements due to either evaporation of working liquid from the porous sample(s) or condensation of moisture onto them because the samples are not tightly enclosed when weighed; and the fact that the drying device is situated directly above the balance, which renders it unavailable to heating.

SUMMARY OF THE INVENTION

According to the present invention there is provided a porosimeter apparatus for studying porous material, comprising sample holding means for holding samples of the porous material; a clamping device for compressing said samples; a weighing unit; drying devices for drying said samples; means for passing a drying gas through said drying devices; a heater for heating said drying gas; and an automatic manipulator for transferring said sample holding means between the drying devices and the weighing unit; and wherein the distance between each drying device and the weighing unit is sufficient to prevent damage to the weighing unit by the heated drying gas.

The distance between the drying devices and the balance should be sufficient, preferably 200–599 mm, to prevent damage of the latter when heating the drying gas and thereby emptying the fine pores.

In one embodiment, each drying device consists of a bottom base and a cap or cylinder closed from the top, which tightly covers samples during the process of drying and uncovers them aftermath. The top cylinder contains a tube for the drying gas and moves up or down under the action of a pneumatic drive.

The cap or cylinder is closed from the top, thereby tightly covering one or multiple sample frames prior to weighing, and by this means essentially reducing evaporation of measuring liquid or condensation of moisture during weighing. Thus, the accuracy of measurements is increased. After weighing, the cylinder rises from the balance. The cylinder or cap goes up or down under the action of a pneumatic drive.

A manipulator having two degrees of freedom may be used. This manipulator is capable of performing both vertical and horizontal motions, the former being necessary for placing sample frames on and removal from the balance pan and the latter for transfer of the frames from the drying chambers to the pan.

The manipulator consists of a horizontal electric servo-driver and a vertical pneumatic drum. The horizontal electric servo-driver works on the "ball-screw" principle and provides good accuracy.

The manipulator contains a gripper for holding the sample frames. The gripper supports the frames from the bottom and does not touch standards and samples.

Vertical servo-drivers may be used for each drying station, which provide vertical positioning of the sample frames while captured by the gripper.

The porosimeter contains a heater of the drying gas (12, FIG. 2).

The porosimeter may contain thermocouples (13, FIG. 2) for control of the temperature of the gas.

Electric heaters can be placed inside of the bottom of the base of each drying device. This considerably expands the opportunities to control the process of drying to achieve the capillary equilibrium between standards and samples. Measurement of temperature in this case is carried out by the thermocouples established in the bottom basis.

The porosimeter provides measurements of porous structure at controlled compression of the samples. The control is realized by setting the value of the electric current through the vertical servo-driver.

A stepper motor is used to assure very sensitive control of the flow of the drying gas.

The drying gas may be passed through a humidifier for very slow evaporation of the measuring liquid off the samples. The humidifier comprises a vessel with a pipe inside. The vessel is filled with the same measuring liquid.

The porosimeter can be connected with PC through a USB port. This port is hot swapping, high-speed and does not require application of powerful and expensive processors.

The automated porosimeter in accordance with embodiments of the invention may have the following advantages over the porosimeter described in U.S. Pat. No. 6,298,711:

1. As a result of using multiple drying devices and heating of gas during drying the speed of measurement has increased.
2. The measurement range has extended to the micro-pore range due to the elevated temperature of the drying gas, which allows drying the micro-pores. A special heater is used to heat the drying gas. All this is achieved by removal of the drying systems from the balance. Therefore the temperature of the balance does not depend on the drying temperature, which can be high enough.
3. The longevity of the standards and balance essentially increases because the gripper supports sample frames from the bottom and touches no standards and samples. It guarantees gentle placing of frames onto the balance by the manipulator (instead of the rougher handling, as in U.S. Pat. No. 6,298,711).
4. The accuracy of the measurements is considerably improved because the porosimeter employs a cap or cylinder closed from the top, which tightly covers each sample or standard before weighing, thereby essentially reducing both evaporation of measuring liquid and condensation of moisture into the pores during weighing.
5. The high accuracy of measurements is also provided by using of stepper motors in the automatic flow-metering valve for drying gas, providing a very sensitive control of the drying process.

BRIEF DESCRIPTION OF THE DRAWINGS

The invention will now be described in more detail, by way of example only, with reference to the accompanying drawings, in which.

DETAILED DESCRIPTION OF THE PREFERRED EMBODOMENTS

Figure 1:
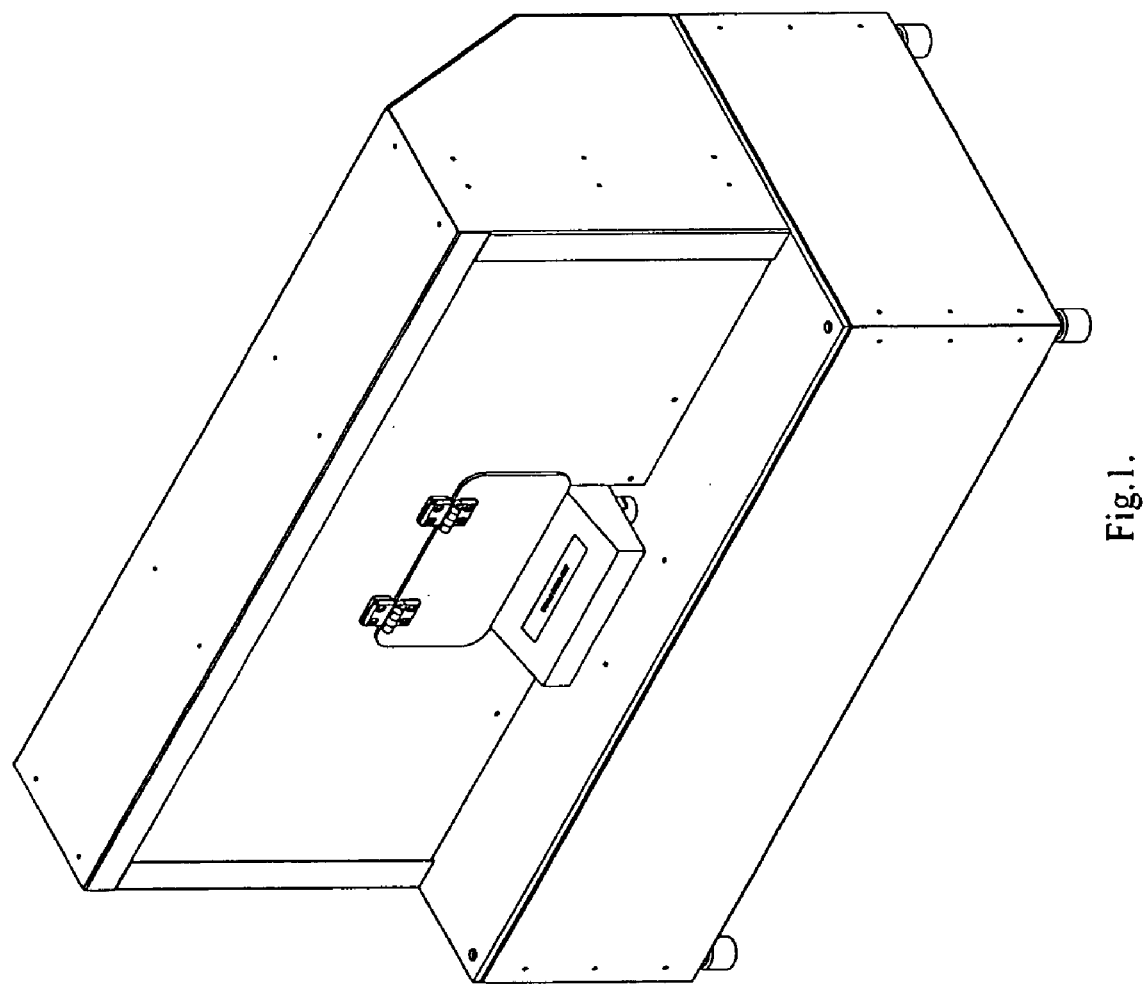
FIG. 1 is a perspective view of a porosimeter apparatus in accordance with one embodiment of the invention.

In the accompanying drawings, the reference numerals have the following significance:
1. Manipulator horizontal servo,
2. Manipulator vertical cylinder,
3. Manipulator gripper,
4. Balance,
5. Balance cover,
6. Drying station,
7. Frames, 8. Spring holder,
9. Sample,
10. Standards,
11. Vertical electrical servo,
12. Electrical heating cartridge,
13. Thermocouple sensor,
14. Electrical heater in the bottom basis,
15. Clamping device,
16. Tube for gas,
17. Pneumatic drive.

The automated standard porosimeter in accordance with embodiments of the invention is based on the Method of Standard Porosimetry (USSR Inventors Certificate No. 543852, 1975, G01N15/08; Yu. M. Volfkovich, V. S. Bagotzky, J. Power Sources, 48 (1994) 327, 339), and the porosimeter described in U.S. Pat. No. 6,298,711, the contents of which are herein incorporated by reference.

Figure 5:
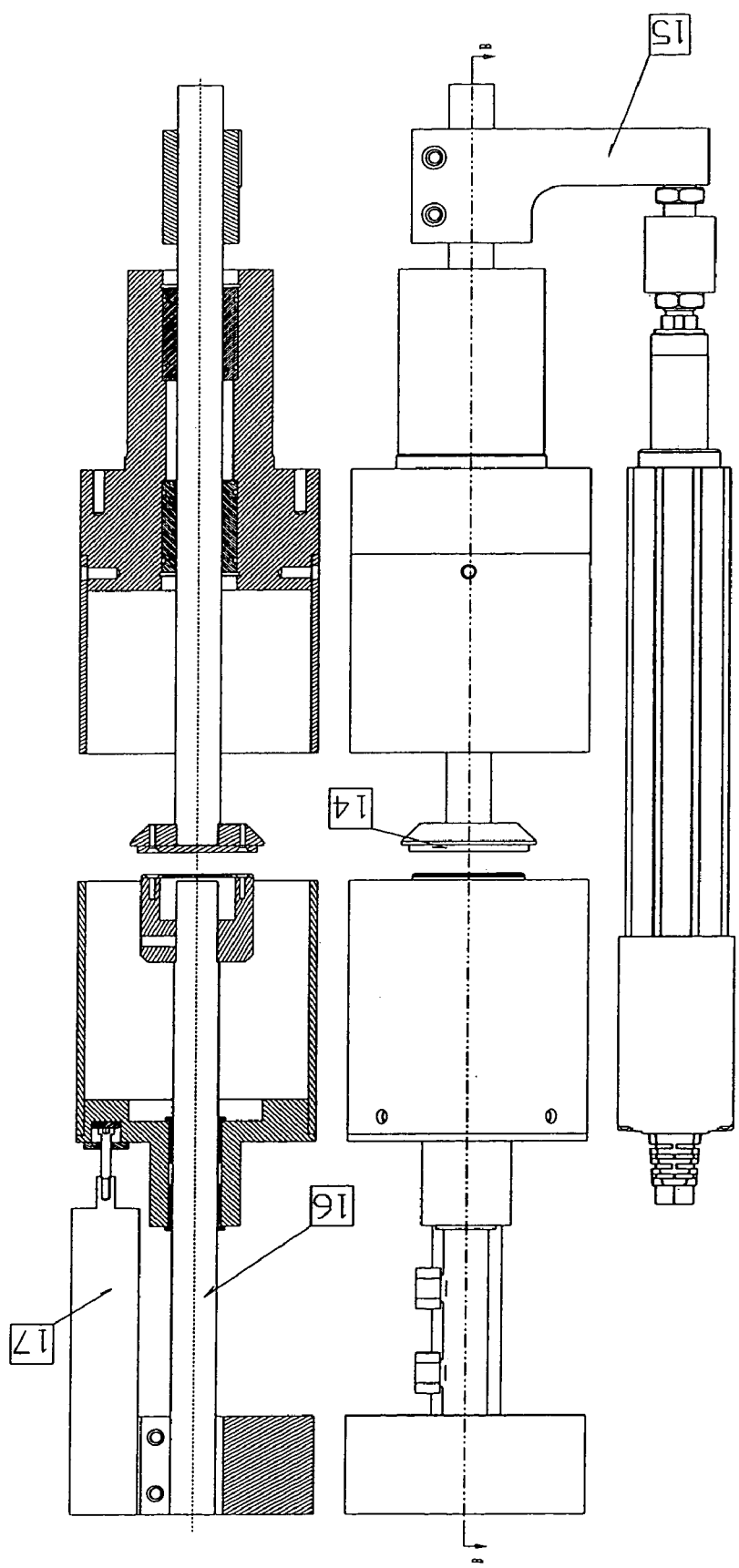
FIG. 5 is a detailed view of the clamping device and heater.

The porosimeter (FIG. 1) comprises: a clamping device (15, FIG. 5) for applying pressure to the standards (10, FIG. 3) or sample(s) (9, FIG. 3), holders and frames for the samples (7), an automatic manipulator (1,2,3) for moving of the holders with samples, drying devices (6,12,14), an automatic flow-meter valve for gas and electric drivers of the manipulator (1).

Figure 3:
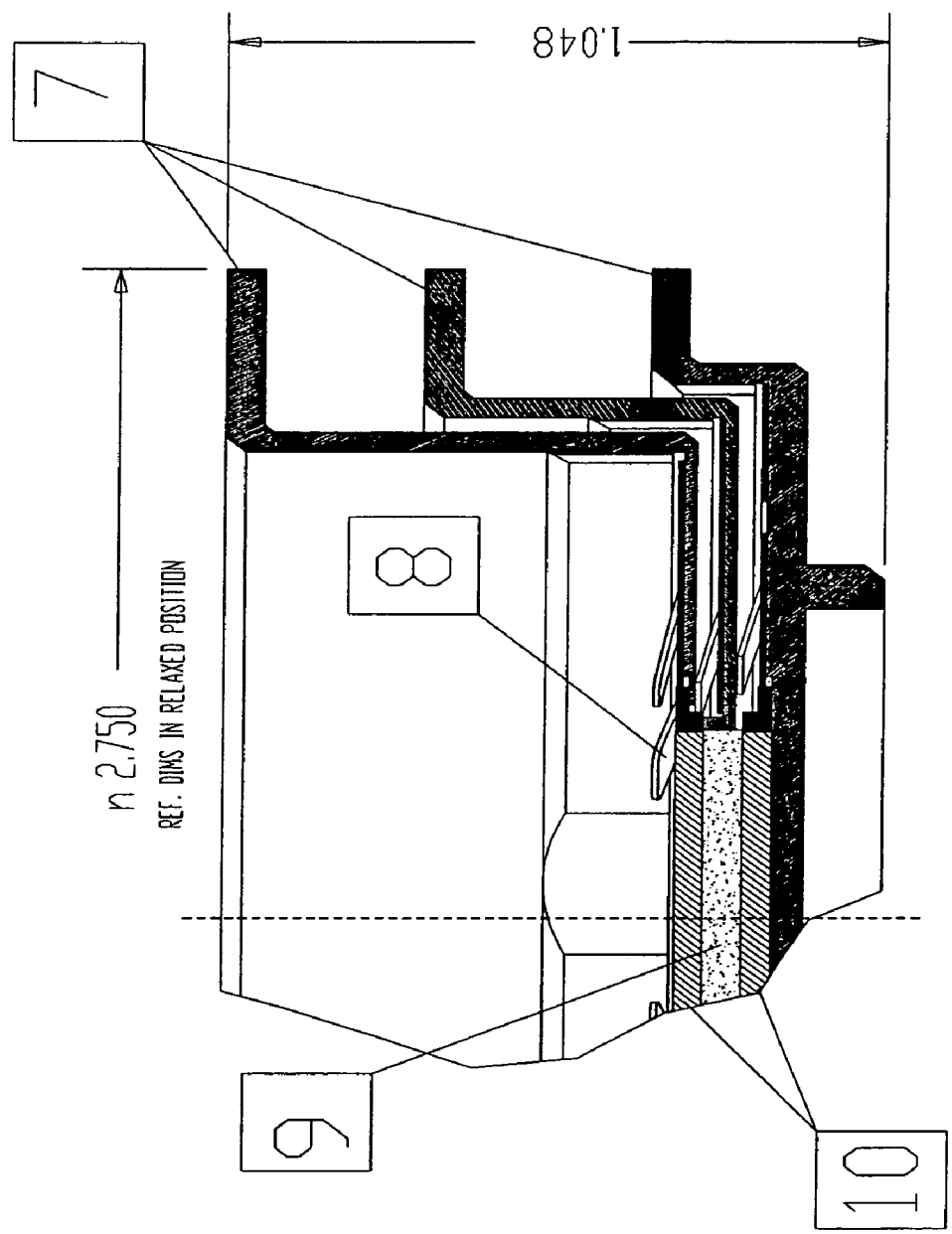
FIG. 3 is a detailed view of the sample holders end flames.

As shown in FIG. 3, the samples 9 are mounted in the spring holders 8 within the dishes 7, referred to as frames. The frames and holders together comprise holding means for the samples. The holders 8 can also contain standard samples 10 for comparison purposes.

As partly shown in FIG. 1, the automated porosimeter (ASP) comprises two drying stations 6 with adjustable compression force, a precision electronic balance 4, a manipulator to transfer samples between drying stations and the balance, two heaters for a drying gas, four flow-metering stations to provide controllable drying gas flow and to create proper gas atmosphere inside the machine, a computer, a display, and two sets of sample frames (three in each).

Each of two drying station provides flow of gas around the surface of the top standard.

The distance between each drying device and the balance in this embodiment is 220 mm.

The temperature of the drying gas can be set between 20 and 100° C. The samples can be compressed with the clamping device 15 by using controllable pressure up to 30 20 kgf/cm$^2$. Sample frames (7, FIG. 3) have spring holders (8. FIG. 3) that also help to separate samples (9, FIG. 3) from one another prior to weighing in order to avoid extra redistribution of liquid between the samples and the standards (10, FIG. 3).

The weighing unit in the form of an electronic balance (4, FIG. 2, 5) has an accuracy of 0.1 mg and maximum weight 200 g. It sends the information to the computer when the weight is stabilized. To get a proper reading, the balance must be protected from the outside environment. For this purpose the balance cover (5, FIG. 2, 4) closes the samples during weighing.

Figure 2:
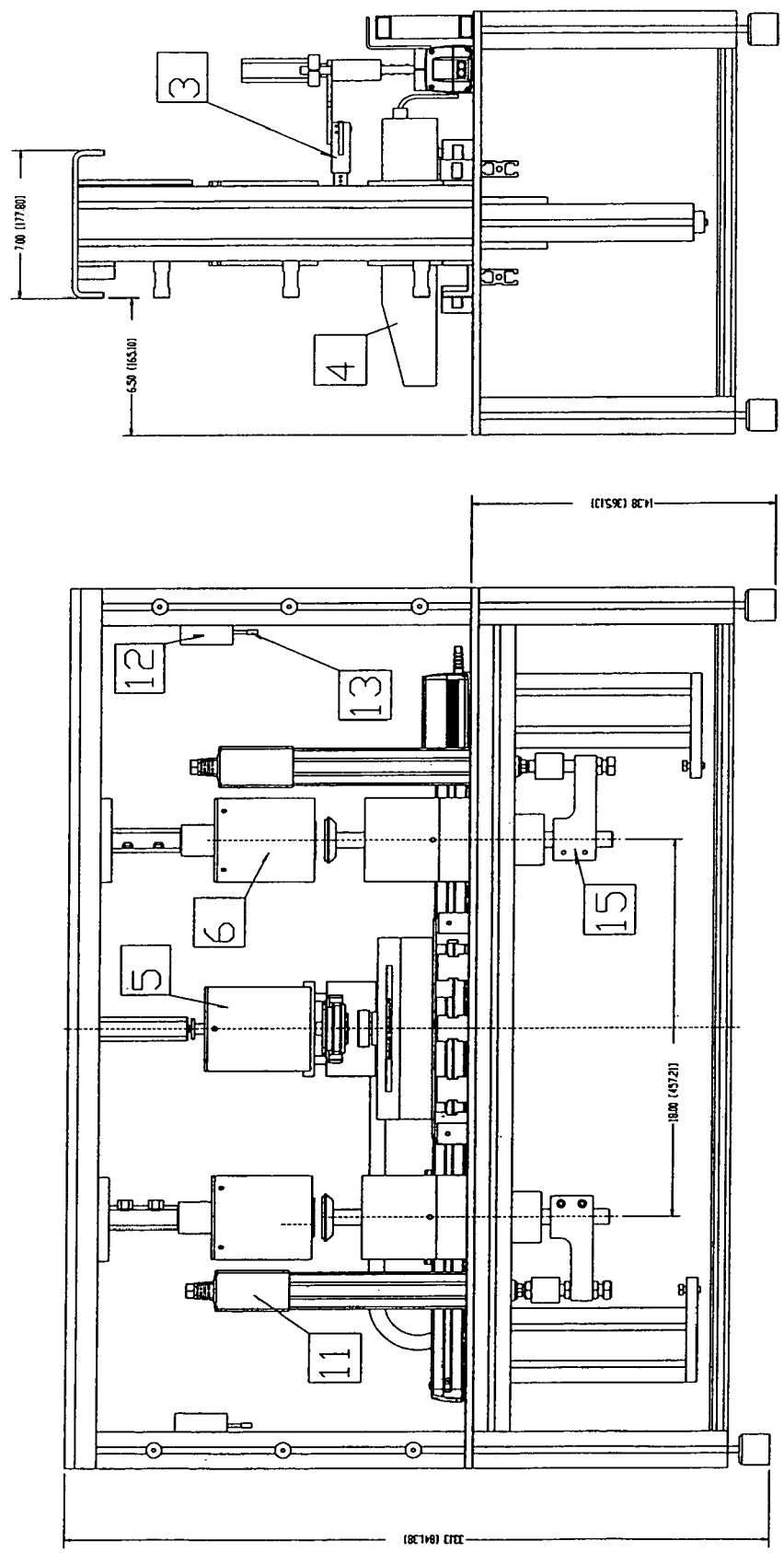
FIG. 2 is a front view of the drying devices and balance unit.
Figure 4:
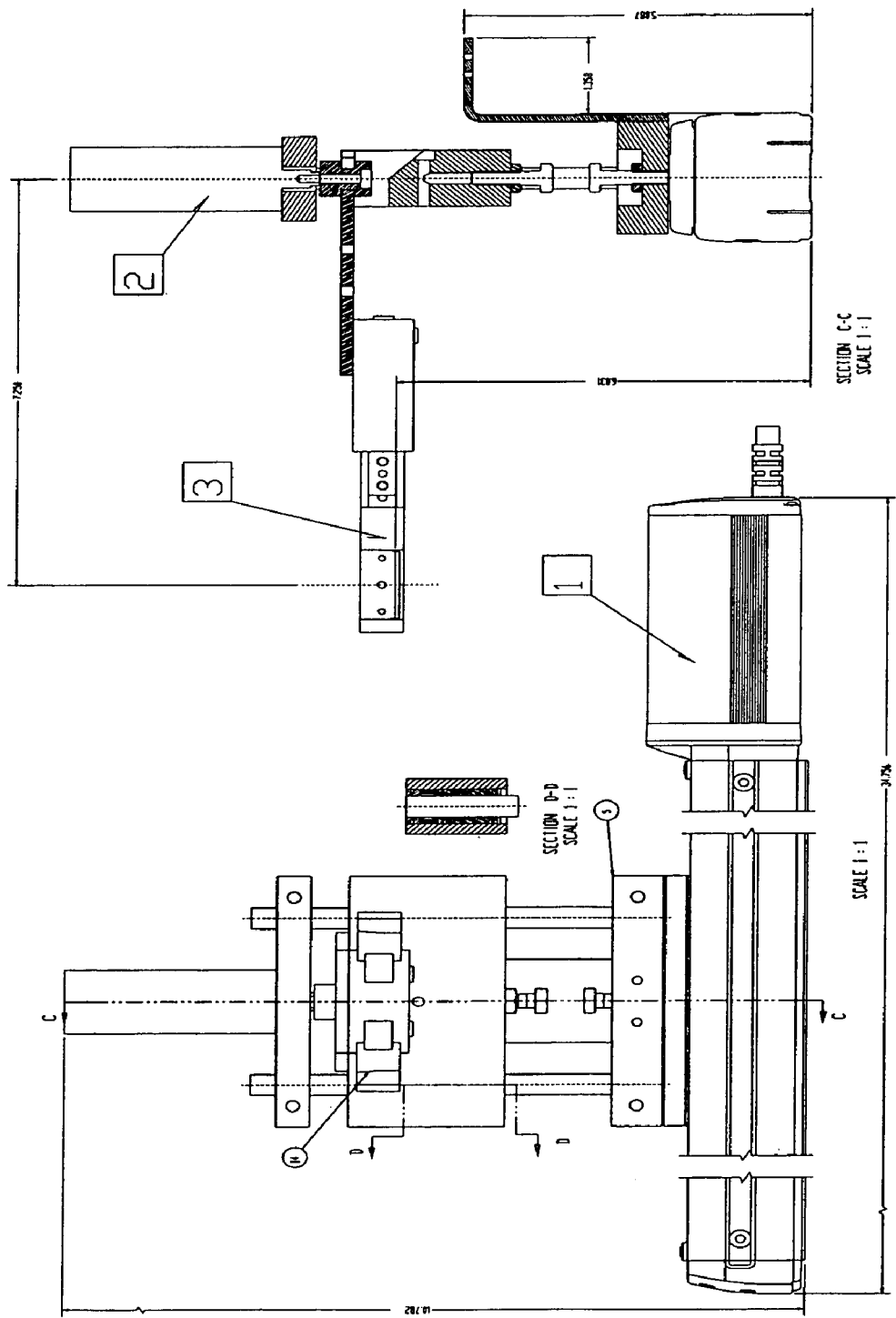
FIG. 4 is a detailed view of the manipulator.

The manipulator (3, FIG. 2,) provides the transfer of frames in quantity of one, two or three between the left and right drying stations (6, FIG. 2,) and the balance (4, FIG. 2,). It utilizes the horizontal electrical servo drive (1, FIG. 2,), vertical pneumatic cylinder (2, FIG. 4) and the pneumatic gripper with specially designed jaws (3, FIG. 2,). The mechanical setup of the machine gives the opportunity to select the number of simultaneously transferred samples simply by changing the height of the dryer position at the moment of load/unload. The dryer position can be set by the vertical electrical servo with controlled force (11, FIG. 2,).

The Jaws (3, FIG. 2, 4) hold sample frames (7, FIG. 3) from the bottom, thereby no force is applied to the frame and no force is applied to the balance (4, FIG. 2) at the moment of placing or pickup.

The flow control stations use stepper motors working together with precision metering valves. The station provides up to 7000 increments of the flow from fully closed to 900 SCFH. The valve has 20 turns and can be rotated at the speed of 30 rpm (10 seconds from fully closed to fully open). During homing of stepper motors the flow is closed by the special pneumatic valve.

The machine utilizes compressed dry nitrogen for both drying and motion. The input pressure must be in a range from 55 to 200 psi (3.7 to 14 bars). The machine has 40 mkm filter and pressure regulator to provide the proper gas quality.

The gas heater uses an electrical heating cartridge (200VA) mounted in an aluminum block (12, FIG. 2) The block has a 100-mm path for the gas and the thermocouple sensor (13, FIG. 2). The software provides the +/−1.5° C. accuracy of the block temperature. The heater is placed between the flow control station and the drying station so that the gas flow through the heater is small and the gas can be heated properly. Each side has its own flow control station and heater in order to provide the independent control of the drying process.

Two additional flow control stations can be used to generate the proper internal atmosphere inside the machine (humid or dry).

The computer is connected to the machine through a USB cable. Inside the machine the USB interface splits into four independent serial ports (RS232 and RS485) that control all internal automation. The software is written in Visual Basic and can be simply upgraded. The machine runs under Windows 2000Pro but it can use any Windows OS (98, NT4.0, 2000, ME, XP).

All hardware used in the machine does not have any fans or other constantly moving/rotating parts in order to provide quiet environment for the precision scale. All parts are mounted on the solid aluminum base plate and frame that also helps to improve the scale performance.

The sample holders are designed to provide the contact between samples and standards regardless of the average sample thickness. The maximum sample thickness is limited to 5 mm. Larger values can be processed but it requires position adjustment of the manipulator.

The spring ring that holds the sample in the frame also has flaps that push away the top frame when the stack is not compressed. It effectively disconnects samples from one another prior to weighing in order to avoid redistribution of the liquid between the samples and the standards after the stack is disassembled.

The diameter of frames is chosen so that the gripper holds any frame from the bottom without compressing it. It guarantees gentle placing of frames onto the balance by the manipulator.

The set of frames can be replaced because the system measures their weight prior to each process.

4. Modes of Operation

The ASP provides a consistent process for drying, balancing and weighing samples and standards without human interference starting from the fully filled samples up to almost dry conditions. In order to speed up the measurements, the ASP has two drying stations that can be programmed and run independently.

The ASP drying stations can use dry or wet gas at normal or elevated temperature. The flow, temperature, and time of drying are controlled by the software and can be adjusted through the setup file.

Only the first steps—weighing of the glass dry samples, standards and frames—have to be done with the help of the operator. After the samples and standards are filled under vacuum with liquid and placed in the frames, the ASP performs the rest of the process automatically.

The ASP machine has two main modes of operation: Preparation and Measurement. The Preparation procedure includes:

Setup of measurement parameters (standards selection, parameters setup, etc.)
Weighing the vial
Weighing the dry samples and the standards in vials
Filling up the samples and the standards with liquid under vacuum
Weighing the empty frames, and
Assembling the frames with standards and samples The operator performs these steps under the control of the software—the computer tells operator what to do and stores the results of weighing in proper variables.

After all filled samples and standards are mounted in frames and placed on the balance, the operator starts the Measurement process. The machine places the samples and standards into one of the drying stations and starts the automatic measurement procedure. All current results are shown on the screen.

In addition to these main modes, the maintenance mode helps to adjust machine parameters (positions, speeds, timing, etc.), to check sensors and components.

After power up, the machine requires initial homing. This process takes approximately a minute—all servos and stepper drives have to be homed, all pneumatic actuators must be initialized. In order to proper react on homing events, the computer performs homing of one station at a time.

General Procedures

Power Up and Homing

Before switching the electrical power on, the machine has to be connected to the dry compressed nitrogen source. The main shut-off valve must be closed.

After the gas is connected, the operator opens the main shut-off valve and checks the pressure level. All pneumatic actuators will go to their home position: all cups must be raised; the gripper is closed and raised.

The operator connects the machine to 110VAC and switches the main power switch on. All drives must stay still at this moment. Magnetic sensors on pneumatic components must indicate the correct position. Switch the balance power on by pressing the button on the scale.

The operator then powers up the computer and connects it to the machine by the USB cable. After the computer is ready, one should see the main window of the Porosimeter program with the Home button on it.

The operator removes all frames from the machine and presses the Home button. During homing, he will see the movements of servo drives and hear some noise from inside the machine generated by the stepper drives moving home. The process of homing can be monitored from the message window on the computer screen. When the message "SYSTEM IS READY!" appears the operator can start the process.

Setting Up Parameters

There are two sources of process parameters that can be set—the SETUP.INI file and the initial dialog of the System.Process parameters that are common for most of measurement sessions are stored in the SETUP.INI file. For example: the time interval between checking the weight of samples, the parameters of the function to determine the drying temperature and flow, etc.

The program dialog allows the operator to select the top and bottom standards parameter files, the result file name, the geometry of the samples, the density of the liquid, etc. This dialog opens for each station separately giving the opportunity to measure two completely different samples simultaneously.

After setting necessary parameters the program asks to measure the weight of the empty vials used for each sample.

Weighing the Vials

The operator has to put the vial mentioned on the screen message on the balance, close the balance door and click the button. The system measures the weight and stores the value in a proper internal variable. Altogether the operator has to weigh three vials: for the top standard, for the sample and for the bottom standard.

Weighing the Dry Sample in a Vial

The next step is to measure the weight of the dry sample and the standards. The operator has to put the dried sample and standards into the proper vials, close it and put on the balance in correct order clicking the button. The System will calculate the dry sample and standards weight by subtracting the weight of the vial.

Weighing the Frames

Now operator has to fill up the dry sample and standards in vacuum with a liquid. During this time operator will weigh the frames. This time operator simply assembles the stack of empty frames, puts it on the balance and clicks the button. The machine will use its manipulator to measure all frames in sequence and will leave the stack on the pan.

Filling up Samples and Inserting Samples into Frames

The sample(s) and standards must be filled with a liquid under vacuum using special equipment. When installing sample(s) and standards into frames it is important to remove the extra liquid film and at the same time not to dry samples prior to assembly. The operator has to put the assembled frames onto the balance and click the button. The process starts.

Measurements

The process of measurement in general consists of the following steps: Drying process starts with current flow and temperature set for some time interval. Periodically measurements of the weight of samples and standards and determine how the drying process is going on and whether all samples and standards are in equilibrium. According to the obtained results the system automatically changes the drying temperature and flow and, if necessary, the time interval.

When the final conditions of the process are fulfilled, the System puts the frames onto the scale and sends the message on the screen to the operator.

EXAMPLE 2

In a second embodiment of the invention the electric heaters are placed inside the bottom base of each drying device carry out heating of samples and standards in it. In this case the heat flow is transferred to a sample and standards through aluminum frame. Measurement of temperature in this case is carried out by the thermocouples fixed on the top surface of bottom base.

The described automated porosimeter offers the possibility to obtain a great amount of information, namely: pore volume distribution in term of the pore radii in the range from ~0.3 to $3 \times 10^5$ nm; average pore radius; specific pore volume (porosity); specific surface area in the range from ~$10^{-3}$ to $5 \times 10^{+3}$ m$^2$/cm$^3$; pore surface distribution in term of the pore radii in the range from ~1 nm to $3 \times 10^5$ nm; liquid distribution in term of the free binding energy liquid-sample in the range~from $10^{-5}$ to 10 kJ/mole; liquid distribution in term of the capillary pressure in the range~from $10^4$ to $10^{10}$ dyne/cm$^2$; desorption (adsorption) isotherm; wetting angle and its dependence on pore radius; different properties of multicomponent hydrophilic-hydrophobic bodies (in this case water and octane or another liquid with wetting angle about zero for any sample, are used as measuring liquids), etc.

What is claimed is:

1. A porosimeter apparatus for studying porous material, comprising:
    sample holding means for holding samples of the porous material;
    a clamping device for compressing said samples;
    a weighing unit;
    drying devices for drying said samples;
    means for passing a drying gas through said drying devices;
    a heater for heating said drying gas; and
    an automatic manipulator for transferring said sample holding means between the drying devices and the weighing unit; and
    wherein the distance between each drying device and the weighing unit is sufficient to prevent damage to the weighing unit by the heated drying gas, and wherein said manipulator has two degrees of freedom, said manipulator being capable of performing both vertical and horizontal motions, the former being for placing said sample holding means on, and removing said sample holding means from, the weighing unit, and the latter for transferring said sample holding means between the drying devices and said weighing unit.

2. The porosimeter apparatus according to claim 1 which is configured to provide measurement of the porous structure at controlled compression of the samples by setting the value of the electric current through the vertical servo-driver.

3. The porosimeter apparatus according to claim 1 further comprising a stepper motor for ensuring sensitive control of the flow of the drying gas.

4. The porosimeter apparatus according to claim 1 wherein said distance between each drying device and the weighing unit is 200–500 mm.

5. The porosimeter apparatus according to claim 1 wherein each drying device consists of a base and a cap closed at the top, which cap tightly covers samples during the process of drying and uncovers them afterwards, and wherein the cap contains a tube for the drying gas.

6. The porosimeter apparatus according to claim 5 wherein said heater is an electric heater placed inside of the base of each drying device.

7. The porosimeter apparatus according to claim 6 further comprising thermocouples fixed on the top surface of said base for measuring temperature.

8. The porosimeter apparatus according to claim 5 wherein the cap of each drying device is displaceable up or down under the action of a pneumatic drive.

9. The porosimeter apparatus according to claim 8 wherein the cap is closed at the top, thereby tightly covering one or multiple sample frames prior to weighing.

10. The porosimeter apparatus according to claim 9 wherein said cap is displaceable longitudinally under the action of a pneumatic drive.

11. The porosimeter apparatus according to claim 1 wherein said manipulator comprises a horizontal electric servo-driver and a vertical pneumatic drum.

12. The porosimeter apparatus according to claim 11 wherein the horizontal electric servo-driver is of the "ball-screw" type.

13. The porosimeter apparatus according to claim 11 wherein said manipulator comprises a gripper for gripping the sample holding means.

14. The porosimeter apparatus according to claim 13 wherein the gripper supports the sample holding means from the bottom and does not touch the samples therein.

15. The porosimeter apparatus according to claim 13 wherein the manipulator includes vertical servo-drivers for each drying station, said vertical servo drivers providing vertical positioning of the sample frames while captured by the gripper.

16. The porosimeter apparatus according to claim 15 further comprising thermocouples for controlling the temperature of the drying gas.

* * * * *